United States Patent
Yamaura

(10) Patent No.: US 8,431,697 B2
(45) Date of Patent: Apr. 30, 2013

(54) TRIALLYL ISOCYANURATE, TRIALLYL CYANURATE AND PROCESS FOR PRODUCING TRIALLYL ISOCYANURATE

(75) Inventor: Mabuko Yamaura, Fukushima-ken (JP)

(73) Assignee: Nippon Kasei Chemical Company Limited, Iwaki-shi, Fukushima-ken (JP)

( * ) Notice: Subject to any disclaimer, the term of this patent is extended or adjusted under 35 U.S.C. 154(b) by 0 days.

(21) Appl. No.: 13/287,270

(22) Filed: Nov. 2, 2011

(65) Prior Publication Data
US 2012/0095223 A1  Apr. 19, 2012

Related U.S. Application Data

(63) Continuation-in-part of application No. PCT/JP2010/058565, filed on May 20, 2010.

(30) Foreign Application Priority Data

May 25, 2009  (JP) ................ 2009-125333

(51) Int. Cl.
| C07D 251/34 | (2006.01) |
| C07D 251/26 | (2006.01) |
| C07D 239/30 | (2006.01) |
| C07D 239/34 | (2006.01) |

(52) U.S. Cl.
USPC ........... 544/221; 544/215; 544/219; 544/298; 544/334

(58) Field of Classification Search ............ 544/221
See application file for complete search history.

(56) References Cited

U.S. PATENT DOCUMENTS

| 2,537,816 | A | | 1/1951 | Dudley |
| 3,322,761 | A | * | 5/1967 | Little Edwin D ............. 544/221 |
| 8,198,431 | B2 | * | 6/2012 | Werle et al. ................... 540/145 |
| 2009/0312545 | A1 | | 12/2009 | Werle et al. |

FOREIGN PATENT DOCUMENTS

| JP | 47-22588 | 6/1972 |
| JP | 48-26022 | 8/1973 |
| JP | 11-255753 | 9/1999 |
| WO | WO 2008/006661 | 1/2008 |

OTHER PUBLICATIONS

English language translation of the International Preliminary Report on Patentability and Written Opinion in PCT/JP2010/058565 dated Dec. 22, 2011.
International Search Report for PCT/JP2010/058565, mailed Aug. 10, 2010.

* cited by examiner

*Primary Examiner* — Venkataraman Balasubramanian
(74) *Attorney, Agent, or Firm* — Nixon & Vanderhye P.C.

(57) ABSTRACT

The present invention provides triallyl isocyanurate comprising a less amount of corrosive substances by identifying the corrosive substances among impurities included in the triallyl isocyanurate. Triallyl isocyanurate of the present invention comprises an organic chlorine compound represented by the following general formula (I) in an amount of not more than 100 ppm:

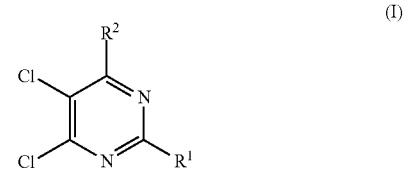

(I)

wherein $R^1$ and $R^2$ are respectively a chlorine atom or an allyoxy group with the proviso that at least one of $R^1$ and $R^2$ is a chlorine atom.

10 Claims, No Drawings

TRIALLYL ISOCYANURATE, TRIALLYL CYANURATE AND PROCESS FOR PRODUCING TRIALLYL ISOCYANURATE

This application is a Continuation-In-Part of International Application No. PCT/JP2010/058565 filed May 20, 2010 which designated the U.S. and claims priority to JP Patent Application No. 2009-125333 filed May 25, 2009, the entire contents of each of which are hereby incorporated by reference.

TECHNICAL FIELD

The present invention relates to triallyl isocyanurate, triallyl cyanurate and a process for producing the triallyl isocyanurate. The triallyl isocyanurate is hereinafter referred to merely as "TAIC".

BACKGROUND ART

TAIC may be produced, for example, according to the following reaction route in which 2,4,6-trichloro-1,3,5-triazine (cyanuric chloride) is reacted with allyl alcohol to obtain triallyl cyanurate (hereinafter referred to merely as "TAC") (Non-Patent Document 1), and then the thus obtained TAC is subjected to rearrangement reaction (Patent Document 1).

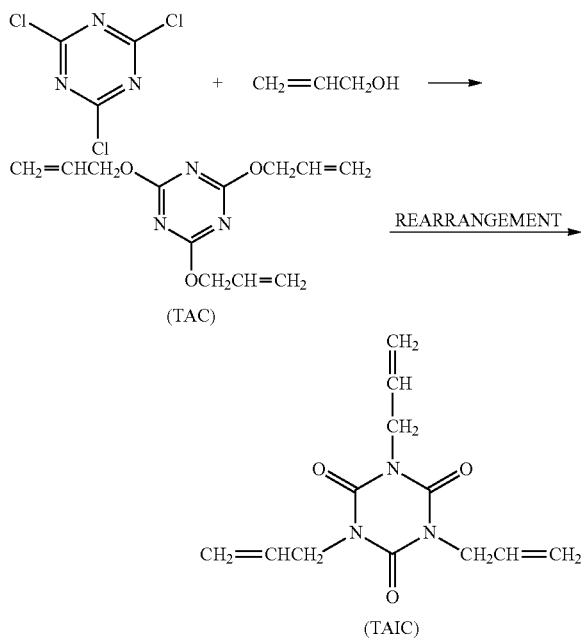

TAIC is useful as a crosslinking agent having excellent heat resistance and chemical resistance, and it is expected to use TAIC in extensive applications such as electronic materials, liquid crystals, semiconductors and solar cells. For example, in printed circuit boards, i.e., plate- or film-shaped members constituting electronic circuits in which a number of electronic parts such as integrated circuits, resistors and capacitors are fixed on a surface thereof and connected to each other through wirings, there is proposed the method in which TAIC is used as a sealing material for preventing penetration of substances such as liquids and gases into the respective electronic parts (Patent Document 2). In such a proposed method, TAIC is used as a liquid sealing material because the TAIC is present in the form of a viscous liquid (melting point: 26° C.) at an ordinary temperature. In addition, in order to enhance a wettability of TAIC, a silane coupling agent is added thereto. Also, TAIC is used as a crosslinking agent for crosslinkable polymers (Patent Document 3).

Meanwhile, although there is no report for impurities included in TAIC obtained by the above rearrangement of TAC, the impurities which may cause metal corrosion must be removed from TAIC to reduce their content to a level as small as possible.

PRIOR DOCUMENTS

Non-Patent Documents

Non-Patent Document 1: "JACS", Vol. 73, 2986-2990 (1951)

Patent Documents

Patent Document 1: Japanese Patent Publication (KOKOKU) No. 4-6570
Patent Document 2: Japanese Patent Application Laid-Open (KOKAI) No. 2007-115840
Patent Document 3: Japanese Patent Application Laid-Open (KOKAI) No. 2006-036876

SUMMARY OF THE INVENTION

Problems to be Solved by the Invention

The present invention has been accomplished in view of the above conventional problems. An object of the present invention is to provide TAIC having a less content of corrosive substances by identifying the corrosive substances among impurities included therein.

Means for Solving Problems

As a result of the present inventors' earnest study for achieving the above object, the following knowledges have been attained.

(1) Impurities in TAIC are derived from impurities in TAC as a raw material of TAIC. The impurities included in TAC are represented by the following chemical formulae (I), (II) and (III).

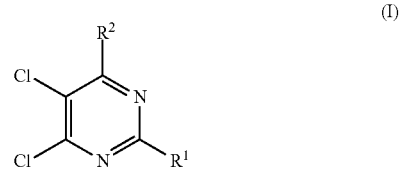

(I)

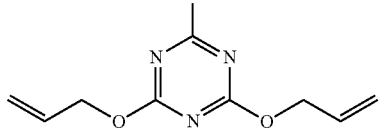

(II)

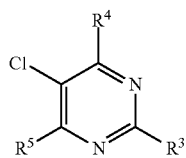
(III)

In the chemical formula (I), $R^1$ and $R^2$ are respectively a chlorine atom or an allyloxy group with the proviso that at least one of $R^1$ and $R^2$ is a chlorine atom. In the chemical formula (III), optional one of $R^3$, $R^4$ and $R^5$ is a chlorine atom, and optional two of $R^3$, $R^4$ and $R^5$ are allyloxy groups.

(2) The compounds represented by chemical formulae (I) and (III) are respectively in the form of an allylated product of chlorinated barbituric acid (2,4,5,6-tetrachloropyrimidine). The reason for production of these compounds is considered as follows. That is, cyanuric chloride is usually produced by trimerization of chlorocyanogen obtained by chlorination of prussic acid. However, if impurities such as acetylene are present in prussic acid as the raw material, tetrachlorobarbituric acid represented by the following chemical formula (IV) is produced. In the reaction between the above 2,4,5,6-tetrachloropyrimidine and allyl alcohol, the organic chlorine compounds represented by the above chemical formulae (I) and (III) are produced as impurities.

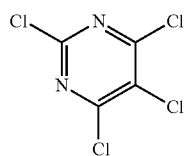
(IV)

(3) It is suggested that the organic chlorine compound represented by the chemical formula (II) is a by-product obtained from the reaction between cyanuric chloride and allyl alcohol.

(4) The organic chlorine compounds represented by the chemical formulae (I) and (II) are gradually hydrolyzed in water to generate chlorine ions which causes corrosion, whereas the organic chlorine compound represented by the chemical formula (III) is subjected to substantially no hydrolysis, and therefore causes no corrosion. Accordingly, the organic chlorine compounds represented by the chemical formulae (I) and (II) are identified to be corrosive substances in TAC.

(5) When TAIC is produced from TAC comprising the organic chlorine compounds represented by the chemical formulae (I) and (II) as the raw material, the organic chlorine compound represented by the chemical formula (I) remains in TAIC as produced, and causes corrosion. That is, the organic chlorine compound represented by the chemical formula (II) is decomposed and removed during the production and purification steps of TAIC, so that the organic chlorine compound represented by the chemical formula (I) becomes substantially only one corrosive substance in TAIC. It is impossible to remove the corrosive substance by water-washing and distillation. However, the corrosive substance can be removed by subjecting it to hydrolysis under specific conditions. When TAC is subjected to rearrangement reaction after thus removing the corrosive substance therefrom, it is possible to produce TAIC having a less content of corrosive substances.

The present invention has been attained on the basis of the above findings and includes a group of mutually related plural inventions, and the aspects of the present invention are as follows.

That is, in a first aspect of the present invention, there is provided triallyl isocyanurate comprising an organic chlorine compound represented by the following general formula (I) in an amount of not more than 100 ppm:

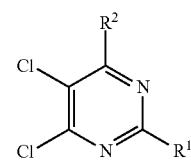
(I)

wherein $R^1$ and $R^2$ are respectively a chlorine atom or an allyoxy group with the proviso that at least one of $R^1$ and $R^2$ is a chlorine atom.

In a second aspect of the present invention, there is provided triallyl cyanurate comprising organic chlorine compounds represented by the following general formulae (I) and (II) in a total amount of not more than 800 ppm:

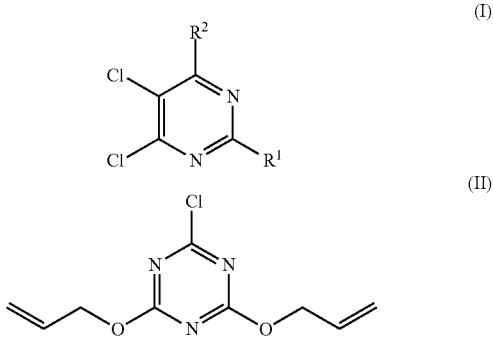

wherein $R^1$ and $R^2$ are respectively a chlorine atom or an allyoxy group with the proviso that at least one of $R^1$ and $R^2$ is a chlorine atom.

In a third aspect of the present invention, there is provided a process for producing the above triallyl isocyanurate, comprising the step of subjecting the above triallyl cyanurate to rearrangement reaction.

In a fourth aspect of the present invention, there is provided a process for producing triallyl isocyanurate, comprising the steps of:

reacting cyanuric chloride with allyl alcohol to obtain triallyl cyanurate;

subjecting the thus obtained triallyl cyanurate to stirring treatment in a strong base aqueous solution having a concentration of 0.5 to 10% by weight at a temperature of 30 to 80° C.; and subjecting the thus treated triallyl cyanurate to rearrangement reaction.

EFFECT OF THE INVENTION

The triallyl isocyanurate according to the present invention is free from occurrence of metal corrosion due to impurities therein, and therefore can be suitably used, for example, as a sealing material for printed circuit boards.

PREFERRED EMBODIMENTS FOR CARRYING OUT THE INVENTION

The present invention is described in detail below.

First, for the sake of explanation, the respective processes for producing TAC and TAIC according to the present invention are described.

The production of the above TAC, i.e., the reaction between cyanuric chloride and allyl alcohol, is carried out under heating in the presence of a basic catalyst (for example, sodium hydroxide). In general, TAC is produced by adding cyanuric chloride to a solution comprising allyl alcohol in an effective amount as a reaction solvent, and given amounts of the basic catalyst and water at room temperature, and then stirring the obtained mixture for a predetermined time. The details of the reaction conditions can be recognized by referring to the above Non-Patent Document 1. The thus obtained crude TAC comprises the organic chlorine compounds represented by the above chemical formulae (I) and (II). The content of the organic chlorine compound represented by the chemical formula (I) in the crude TAC is usually 100 to 250 ppm, whereas the content of the organic chlorine compound represented by the chemical formula (II) in the crude TAC is usually 500 to 1,000 ppm.

In the present invention, in order to selectively hydrolyze the organic chlorine compounds represented by the chemical formulae (I) and (II) without decomposing TAC, the crude TAC is treated in a strong base aqueous solution having a low concentration at a relatively low temperature. More specifically, the treatment of the crude TAC is carried out as follows.

That is, a salt precipitated from a TAC production reaction solution (for example, sodium chloride) is first removed by filtration to recover a filtrate therefrom. The thus recovered filtrate is concentrated to recover a crude TAC as an oily material. Next, the crude TAC (the above oily material) is subjected to stirring treatment in the strong base aqueous solution having a concentration of usually 0.5 to 10% by weight and preferably 1 to 5% by weight at a temperature of usually 30 to 80° C. and preferably 30 to 60° C. The treating time is usually 0.5 to 10 hr and preferably 1 to 6 hr. When the respective treating conditions are less than the above-specified ranges, it may be difficult to hydrolyze the organic chlorine compounds represented by the above chemical formulae (I) and (II). When the respective treating conditions are more than the above-specified ranges, TAC tends to be hydrolyzed.

The production of the above TAIC, i.e., the rearrangement reaction of TAC, is carried out by heat-treating TAC in the presence of a catalyst. The details of the reaction conditions can be recognized by referring to the above Patent Document 1. In the preferred embodiment of the present invention, the rearrangement reaction is carried out in a reaction solvent (for example, xylene) in the presence of a copper catalyst. The reaction temperature is usually 100 to 150° C. and preferably 120 to 140° C. After completion of the reaction, the reaction solvent is distilled off under reduced pressure to recover an oily product. The thus recovered oily product is subjected to distillation under reduced pressure to obtain crystals of TAIC.

Next, TAC according to the present invention is described. TAC according to the present invention is characterized by comprising the organic chlorine compounds represented by the following chemical formulae (I) and (II) in a total amount of not more than 800 ppm.

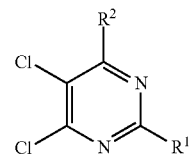

(I)

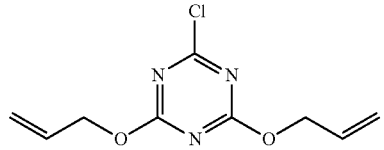

(II)

wherein $R^1$ and $R^2$ are respectively a chlorine atom or an allyoxy group with the proviso that at least one of $R^1$ and $R^2$ is a chlorine atom.

The total content of the organic chlorine compounds represented by the following chemical formulae (I) and (II) in TAC according to the present invention is preferably not more than 500 ppm and more preferably not more than 100 ppm. The TAC according to the present invention can be suitably used, for example, as a raw material for production of TAIC. As a result, it is possible to produce TAIC having a less content of impurities which may cause metal corrosion.

Next, TAIC according to the present invention is described. The TAIC according to the present invention is characterized by comprising the organic chlorine compound represented by the above chemical formula (I) in an amount of not more than 100 ppm. The content of the organic chlorine compound represented by the above chemical formula (I) in the TAIC according to the present invention is preferably not more than 50 ppm and more preferably not more than 30 ppm. The TAIC according to the present invention has a less content of impurities which may cause metal corrosion, and therefore can be suitably used as a sealing material for printed circuit boards. In addition, the TAIC according to the present invention may be mixed with a crosslinkable elastomer and then cured by heating, radiation or the like, and the resulting cured product can be used as a sealing material for electronic materials, semiconductors, solar cell materials, etc. Further, the TAIC according to the present invention may be mixed with a crosslinkable thermoplastic resin and then cured by irradiation with electron beams, etc., and the resulting cured product can be suitably used for coating electric wires, etc.

EXAMPLES

The present invention is described in more detail below by Examples. However, these Examples are only illustrative and not intended to limit the present invention thereto, and various changes or modifications are possible unless they depart from the scope of the present invention. Meanwhile, the analyzing methods used in the following Examples and Comparative Examples are as follows.

(1) Analysis of Organic Chlorine Compounds:

The analysis of the organic chlorine compounds were carried out using a gas chromatograph (by an area percentage method). The conditions for the analysis are shown in Table 1. Meanwhile, a detection limit of the device used was 10 ppm.

TABLE 1

| Device name | "HP6850" manufactured by Agilent Inc. |
|---|---|
| Column name | Capillary column "BPX-5" (60 m × 0.32 mm; film thickness: 0.25 μm) manufactured by SGE Inc. |
| Column temperature | 50° C. (held for 5 min) to 350° C. (at a temperature rise rate of 10° C./min) |
| Injection port temperature | 250° C. |
| Detector temperature | 300° C. |
| Pressure | 150 kPa |
| Split ratio | 20 |
| Solvent | Acetone |
| Concentration of sample | 20% by weight |

Comparative Example 1

A solution comprising 100 g of allyl alcohol, 12 g of NaOH and 10 g of water was mixed with 18.4 g of cyanuric chloride at room temperature. The resulting mixture was stirred at room temperature for 2 hr, and sodium chloride precipitated was removed by filtration to recover a filtrate. The thus recovered filtrate was concentrated to obtain an oily material. Next, the thus obtained oily material was washed with water and then subjected to distillative purification to obtain crystals of TAC (yield: 85%). The thus obtained TAC comprised 170 ppm of a mixture (A) comprising an organic chlorine compound of the chemical formula (I) in which $R^1$ is an allyoxy group and $R^2$ is a chlorine atom (2-allyoxy-4,5,6-trichloropyrimidine) and an organic chlorine compound of the chemical formula (I) in which $R^1$ is a chlorine atom and $R^2$ is an allyoxy group (4-allyoxy-2,5,6-trichloropyrimidine), and 740 ppm of an organic chlorine compound of the chemical formula (II) (2,6-diallyloxy-4-chlorotriazine).

Next, 24.9 g of the above TAC and 3.4 g of cupric chloride hydrate were added to 120 g of xylene, and the resulting mixture was stirred at 120° C. for 2 hr to subject the TAC to rearrangement reaction. Thereafter, the obtained reaction solution was cooled and placed under reduced pressure to distil off xylene therefrom, thereby obtaining an oily material. Next, the thus obtained oily material was subjected to distillation under a reduced pressure of 0.1 Torr at 115° C. to obtain crystals of TAIC (yield: 90%). The thus obtained TAIC comprised 120 ppm of the mixture (A) of the organic chlorine compounds and 10 ppm of the organic compound of the chemical formula (II).

Example 1

The oily material produced in the same manner as defined in Comparative Example 1 was subjected to heating and stirring treatment in a 5% by weight NaOH aqueous solution at 50° C. for 2 hr. Next, the obtained reaction solution was neutralized with hydrochloric acid, and an organic layer was separated therefrom and then subjected to distillative purification to obtain crystals of TAC (yield: 84%). It was confirmed that neither the organic chloride compounds mixture (A) nor the organic chloride compound of the chemical formula (II) were detected in the thus obtained TAC (less than 10 ppm).

Next, the above TAC was subjected to the same procedure subsequent to the rearrangement reaction as defined in Comparative Example 1, thereby obtaining TAIC (yield: 90%). It was also confirmed that neither the mixture (A) of the organic chloride compounds nor the organic chloride compound of the chemical formula (II) were detected in the thus obtained TAIC (less than 10 ppm).

Example 2

The oily material produced in the same manner as defined in Comparative Example 1 was subjected to heating and stirring treatment in a 1% by weight NaOH aqueous solution at 50° C. for 6 hr. Next, the obtained reaction solution was neutralized with hydrochloric acid, and an organic layer was separated therefrom and then subjected to distillative purification to obtain crystals of TAC (yield: 84%). It was confirmed that the thus obtained TAC comprised 40 ppm of the mixture (A) of the organic chloride compounds and 10 ppm of the organic chloride compound of the chemical formula (II).

Next, the above TAC was subjected to the same procedure subsequent to the rearrangement reaction as defined in Comparative Example 1, thereby obtaining TAIC (yield: 90%). It was confirmed that the thus obtained TAIC comprised 10 ppm of the organic chloride compounds the mixture (A), but no organic chloride compound of the chemical formula (II) was detected therein (less than 10 ppm).

Experimental Example 1

Hydrolysis Test of TAIC

A Teflon (registered trademark) pressure container was charged with 1 g of each of the TAICs obtained in the above Examples, etc., and 20 g of water, and the contents of the container were heated at 120° C. for 200 hr to measure a chlorine ion concentration in water. The measurement of the chlorine ion concentration in water was carried out using an ion chromatograph (column used: "DIONEX Ion Pack AS12A"; eluent used: 2.7 mM—$Na_2CO_3$/0.3 mM—$NaHCO_3$). The detection limit of the measuring device used was 1 ppm. The results are shown in Table 2.

TABLE 2

| Kind of TAIC | Chlorine ion concentration (ppm) |
|---|---|
| Comparative Example 1 | 237 |
| Example 1 | ND (less than 1 ppm) |
| Example 2 | 21 |

Experimental Example 2

Hydrolysis of Corrosive Substance

According to the following procedure, the corrosive substance was synthesized, and subjected to hydrolysis under accelerated conditions.

<Corrosive Substance: Synthesis of 2-allyoxy-4,5,6-trichloropyrimidine>

Into a solution comprising 54.04 g (0.2361 mol) of 2,4,5,6-tetrachloropyrimidine produced by Tokyo Chemical Industry Co., Ltd., 12.93 g (0.3070 mol) of NaOH and 280 g of 1,4-dioxane, were added dropwise 18.01 g (0.3070 mol) of allyl alcohol at 40° C. over 2 hr. Further, the reaction mixture was reacted at 40° C. for 2.5 hr, cooled and then subjected to filtration to distil off dioxane in vacuo. The resulting reaction product was purified by silica gel chromatography (ethyl acetate/n-hexane=1/1), thereby obtaining 53.34 g of 2-allyloxy-4,5,6-trichloropyrimidine (yield: 93.5% by weight). The identification of the reaction product was carried out by GC-MS analysis. For reference, the measurement results of the GC-MS analysis are shown in Table 3 below.

TABLE 3

| | |
|---|---|
| GC-MS (EI mode) | m/e 41, 73, 85, 108, 120, 163, 182, 203, 223, 240 |
| GC-MS (CI mode) | (M + 1) 239 |

<Hydrolysis>

A pressure container was charged with 5 g of the above corrosive substance and 5 g of water, and the contents of the container were heated at 140° C. for 6 days. As a result, it was confirmed that the resulting hydrolyzed product had a chlorine ion concentration of 15% by weight.

What is claimed is:

1. Triallyl isocyanurate containing an organic chlorine compound represented by the following general formula (I) as an impurity in an amount of not more than 100 ppm:

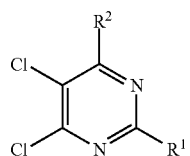
(I)

wherein $R^1$ and $R^2$ are independently a chlorine atom or an allyoxy group with the proviso that at least one of $R^1$ and $R^2$ is a chlorine atom.

2. Triallyl isocyanurate according to claim 1, wherein the triallyl isocyanurate is produced by subjecting triallyl cyanurate to rearrangement reaction.

3. Triallyl cyanurate comprising organic chlorine compounds represented by the following general formulae (I) and (II) in a total amount of not more than 800 ppm:

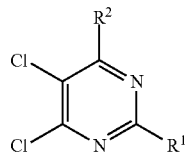
(I)

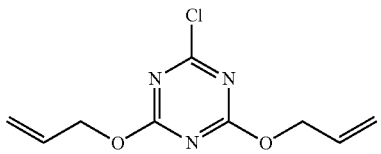
(II)

wherein $R^1$ and $R^2$ are independently a chlorine atom or an allyoxy group with the proviso that at least one of $R^1$ and $R^2$ is a chlorine atom.

4. The process for producing the triallyl isocyanurate as defined in claim 1, comprising the step of subjecting the triallyl cyanurate to rearrangement reaction.

5. The process for producing the triallyl isocyanurate according to claim 4, wherein the triallyl cyanurate is produced by reaction between cyanuric chloride and allyl alcohol.

6. A process for producing triallyl isocyanurate, comprising the steps of:
    reacting cyanuric chloride with allyl alcohol to obtain triallyl cyanurate;
    subjecting the thus obtained triallyl cyanurate to stirring treatment in a strong base aqueous solution having a concentration of 0.5 to 10% by weight at a temperature of 50 to 80° C. for 0.5 to 10 hours; and
    subjecting the thus treated triallyl cyanurate to rearrangement reaction.

7. Triallyl cyanurate according to claim 1, wherein the amount of organic chlorine compound represented by the general formula (I) is not more than 50 ppm.

8. Triallyl isocyanurate according to claim 1, wherein the amount of organic chlorine compound represented by the general formula (I) is not more than 30 ppm.

9. Triallyl cyanurate according to claim 3, wherein the total amount of organic chlorine compounds represented by the general formulae (I) and (II) is not more than 500 ppm.

10. Triallyl cyanurate according to claim 3, wherein the total amount of organic chlorine compounds represented by the general formulae (I) and (II) is not more than 100 ppm.

* * * * *